(12) United States Patent
Reddy

(10) Patent No.: US 10,210,952 B2
(45) Date of Patent: Feb. 19, 2019

(54) SYSTEM AND METHOD FOR PERFORMING AUTOMATED CONTACT AND INFORMATION DELIVERY

(71) Applicant: Karan Reddy, Orlando, FL (US)

(72) Inventor: Karan Reddy, Orlando, FL (US)

( * ) Notice: Subject to any disclaimer, the term of this patent is extended or adjusted under 35 U.S.C. 154(b) by 627 days.

(21) Appl. No.: 14/808,315

(22) Filed: Jul. 24, 2015

(65) Prior Publication Data

US 2016/0026763 A1    Jan. 28, 2016

Related U.S. Application Data

(60) Provisional application No. 62/029,785, filed on Jul. 28, 2014.

(51) Int. Cl.
| | | |
|---|---|---|
| *G06F 15/16* | (2006.01) | |
| *G16H 40/20* | (2018.01) | |
| *H04M 3/42* | (2006.01) | |
| *H04M 3/523* | (2006.01) | |
| *G06F 19/00* | (2018.01) | |
| *H04M 3/51* | (2006.01) | |

(52) U.S. Cl.
CPC ............ *G16H 40/20* (2018.01); *G06F 19/00* (2013.01); *H04M 3/42059* (2013.01); *H04M 3/5232* (2013.01); *H04M 3/5133* (2013.01); *H04M 3/5166* (2013.01); *H04M 2201/42* (2013.01); *H04M 2203/408* (2013.01); *H04M 2203/6009* (2013.01); *H04M 2242/04* (2013.01); *H04M 2242/06* (2013.01)

(58) Field of Classification Search
CPC ............ G06F 19/327; H04M 3/42059; H04M 3/5232; H04M 3/5133; H04M 3/5166; H04M 2201/42; H04M 2203/408; H04M 2203/6009; H04M 2242/04; H04M 2242/06
USPC ..................................................... 379/265.09
See application file for complete search history.

(56) References Cited

U.S. PATENT DOCUMENTS

| | | |
|---|---|---|
| 5,754,111 A | 5/1998 | Garcia |
| 8,332,466 B1 | 12/2012 | Cha et al. |
| 8,385,528 B2 | 2/2013 | Selph et al. |
| 2002/0165732 A1 | 11/2002 | Ezzeddine et al. |
| 2006/0010218 A1 | 1/2006 | Turcotte, II |
| 2010/0094652 A1 | 4/2010 | Dorsett |
| 2011/0153352 A1 | 6/2011 | Semian |

(Continued)

*Primary Examiner* — Ahmad F. Matar
*Assistant Examiner* — Jirapon Intavong
(74) *Attorney, Agent, or Firm* — Jason T. Daniel, Esq.; Daniel Law Offices, P.A.

(57) ABSTRACT

A system and method for performing automated contact and information delivery includes one or more doctor office interface devices, and one or more medical facility interface devices that communicate with a site owner system over a network. The system and method permit a doctor office to designate one or more medical professionals to receive messages about a patient at a medical facility, based on the circumstances of the case. The system and method provide a connect on call module for facilitating direct communication between the facility employee and the identified medical professional utilizing both textual and audio/visual mechanisms without revealing the confidential contact information of the medical professional to the facility employee.

20 Claims, 19 Drawing Sheets

(56) References Cited

U.S. PATENT DOCUMENTS

2012/0290638 A1* 11/2012 Narula .................. G06Q 10/10
 709/203
2012/0315867 A1   12/2012 Davis et al.
2013/0103768 A1*  4/2013 Freebeck ................ H04L 51/36
 709/206
2014/0214876 A1*  7/2014 Wellons ................. G06Q 10/10
 707/758

* cited by examiner

Tennant: Premiere Cardiology — 401
Call Routing Preferences

| Type | Call Type/From/Reason | Default | Override CT | Override CT & CF | Call Description |
|---|---|---|---|---|---|
| Call From | Emergency Room | ☐ | ☐ | | Day Call Physician, Nigh ▶ |
| Call From | Any ICU | ☐ | ☑ | | Day Call Physician, Nigh ▶ |
| Call From | Other | ☑ | ☐ | | Day Call NP/PA, Night C ▶ |
| Call Reason | admission | ☐ | | ☐ | Day Call NP/PA, Night C ▶ |
| Call Reason | Critical Labs | ☐ | | ☑ | Day Call Physician, Nigh ▶ |
| Call Reason | Code Blue | ☐ | | ☑ | Day Call Physician, Nigh ▶ |
| Call Reason | New Consult | ☐ | | ☐ | Day Call NP/PA, Day Ca ▶ |
| Call Reason | Family Wants to Talk | ☐ | | ☐ | Day Call Physician, Nigh ▶ |
| Call Reason | FYI | ☐ | | ☐ | |
| Call Reason | Med Reconciliation | ☐ | | ☐ | |
| Call Reason | Need Orders | ☐ | | ☐ | |
| Call Reason | Other | ☐ | | ☐ | |
| Call Reason | Patient Care | ☑ | | ☐ | |
| Call Reason | Pre-Op Clearance | ☐ | | ☑ | |
| Call Reason | Need Test Results | ☐ | | ☑ | |
| Call Reason | Room Change Notification | ☐ | | ☐ | |
| Call Reason | Cath and or STEMI | ☐ | | ☑ | |
| Call Reason | Stroke Alert | ☐ | | ☑ | |
| Call Type | Doctor to Doctor | ☐ | | | Day Call Physician, Nigh ▶ |
| Call Type | Routine | ☑ | | | Day Call Physician, Nigh ▶ |
| Call Type | STAT | ☐ | | | Day Call Physician, Nigh ▶ |
| Call Type | Urgent | ☐ | | | Day Call Physician, Nigh ▶ |
| Call Type | Urgent IVR Patient Call | ☐ | | | Day Call Physician, Nigh ▶ |
| Call Type | Urgent IVR Pharmacy Call | ☐ | | | Day Call Physician, Nigh ▶ |

Call Description popup (405):
- ☐ 1st on Call
- ☐ 2nd on Call
- ☐ Day Call NP/PA
- ☑ Day Call Physician
- ☐ Day Interventional Call
- ☐ ER Coverage
- ☐ Interventionalist
- ☐ Night Call NP/PA
- ☑ Night Call Physician
- ☐ Night Interventional Call
- ☐ Others

[SAVE] [CLOSE]

Tenant: Premier Cardiology ▸ | ⊙ For Self/Group  ○ For ACO/CIN Service
Patient Location: Orlando Hospital - Princeton/HOP-DAY ▸ | ALL Select Patient Call Group: Select ▸ | Person: Aman, a MD/Cardiology ▸ | Recent | ADD ▸

Message being sent to:  Recording: OFF
Send Box

| Select Selected Person | Covering Person | Status | Call description | Call Group | Actions |
|---|---|---|---|---|---|
| ☐ Aman, a MD | ☐ Coronary, Doctor D.O./Cardiology | On Call | Day International Call | PC South | ＋EPA 📞 ⊖ |
| ☑ Aman, a MD | ☐ Heart, Doctor MD/Cardiology | On Call | Day Call Physician | PC South | ＋EPA 📞 ⊖ |
| ☐ Aman, a MD | ☐ Smith, Mary ARNP/Cardiology | On Call | Day Call NP/PA | PC South | ＋EPA 📞 ⊖ |

605b    614    613

☐ Covering Person Override  ☐ Reply Requested  ☐ Call Back Requested  Call Back Number: 407-467-0824

Call Type (CT): STAT ▸ | Call From (CF): Any KU ▸ | Call Reason (CR):

602    603

INITIATE CONFERENCE  Critical Labs ▸

604

600

SYSTEM AND METHOD FOR PERFORMING AUTOMATED CONTACT AND INFORMATION DELIVERY

CROSS-REFERENCE TO RELATED APPLICATIONS

This application claims the benefit of U.S. Application Ser. No. 62/029,785, filed on 28 Jul. 2014, the contents of which are incorporated herein by reference.

TECHNICAL FIELD

The present invention relates generally to the health care industry, and more particularly to a unified contact platform providing increased communication efficiency between health care providers and staff that integrates a plurality of different communication technologies.

BACKGROUND

The statements in this section merely provide background information related to the present disclosure and may not constitute prior art.

Owing to the misuse and abuse of health care provider contact information, such as a doctor's cell phone number, for example, and in order to preserve the valuable time of the doctor, current human Answering Services and/or Call Centers are in place to manually facilitate communication between care providers. In this regard, Call Centers function to coordinate various receiver preferences like who is on call and how they would like to receive messages pertaining to their patients. However, as each physician group is different, and each physician within the physician groups and/or hospital has their own contact preferences it can be extremely difficult for a care provider (such as a nurse or doctor, for example) to make contact with another care provider in a timely fashion.

To this end, Care Coordination is a vital role of the nursing staff. In order for nurses to be most effective, it is critical that they have access to communication technologies capable of delivering patient information to a care provider in an expedient manner. Currently, nurses spend significant amounts of time using conventional methods of communication trying to reach a physician or send a message. Effective communication helps avoid costly errors, saves time, and allows nurses to deliver the quality care that patients deserve. Ideally, in an emergency situation, the nurse should be able to call the physician directly, update the patient's status, and get instructions regarding the patient care.

Conventional contact methods are highly variable, with each medical staff member employing a unique and often complex algorithm to determine exactly who to contact and then how that physician should be reached at any given moment in time. Accessing physicians requires maintaining multiple phone lists, contact instructions, and call schedules—all of which must be referenced and interpreted with each physician-contact attempt. Breakdowns in communication are commonplace, resulting in thousands of hours of wasted time.

Background FIG. 1 is an exemplary flowchart 10 demonstrating a conventional contact cycle between one care provider (in this instance a nurse) and another care provider (in this instance a Physician). As shown, the typical process can involve upwards of 10 different steps and can take approximately 20 minutes from start to finish. As will be readily apparent to those of skill in the art, such delays in providing patient information can mean the difference between life and death in an emergency situation.

In addition to the problems noted above, there currently exists little to no fully auditable communication methods available in a health care setting to keep track of the various communications happening between care providers. Without this information, it is exceedingly difficult to ensure quality control and best practices are being followed.

Yet another problem revolves around HIPAA compliant communications. Currently, communication about patient care occurs through various channels and methods where patient information is not kept confidential and the messaging method is not secure. This results in HIPAA violation as most of this communication is pertained to patient personal information.

Accordingly, to solve all the inconveniences contained in the state of the art, the present invention provides a unified web enabled platform capable of providing sustained, highly efficient and auditable communication among individuals and entities within a given industry. Such a platform can function to improve work flow and productivity, and can function to decrease errors related to poor communication process.

Additional related systems and/or methods pertaining to non-unified communication methodologies include the following documents, the contents of each of which are incorporated herein by reference: U.S. Pat. Nos. 8,385,528, 5,754,111, and patent publication numbers US-2006-0010218, US-2012-0315867.

SUMMARY OF THE INVENTION

The present invention is directed to a system and method for performing automated contact and information delivery. The system includes one or more doctor office interface devices, and one or more medical facility interface devices that are communicating with a site owner system over a network.

Doctor office contact details are supplied to the site owner system via the doctor office interface, and include a series of call preferences identifying a medical professional to whom messages should be sent upon the occurrence of a specified event or situation. The system can include functionality for delaying delivery of routine messages until the next business day, or other such time designated by the medical professional.

Medical professionals employed by the doctor office can input personal contact details such as cellular, home and office telephone numbers, which can be stored by the system and to which calls from medical facility employees can be routed. However, the actual telephone number will not be displayed to the medical facility employee.

Medical facility employees can utilize a connect on call feature of the site owner system to identify a medical professional to whom patient information needs to be sent, based upon various call information selections. The system will automatically identify the correct medical professional based upon the call preferences of the doctor's office and the received call information selections.

Yet another embodiment of the present invention can include functionality for generating and sending secure textual messages that are HIPAA compliant.

This summary is provided merely to introduce certain concepts and not to identify key or essential features of the claimed subject matter.

BRIEF DESCRIPTION OF THE DRAWINGS

Presently preferred embodiments are shown in the drawings. It should be appreciated, however, that the invention is not limited to the precise arrangements and instrumentalities shown.

FIG. 4A shows an exemplary user interface of the system of FIG. 1.

FIG. 6A shows another exemplary user interface of the system of FIG. 1.

FIG. 6C shows another exemplary user interface of the system of FIG. 1.

FIG. 6D shows another exemplary user interface of the system of FIG. 1.

DETAILED DESCRIPTION OF THE INVENTION

Figure 1:
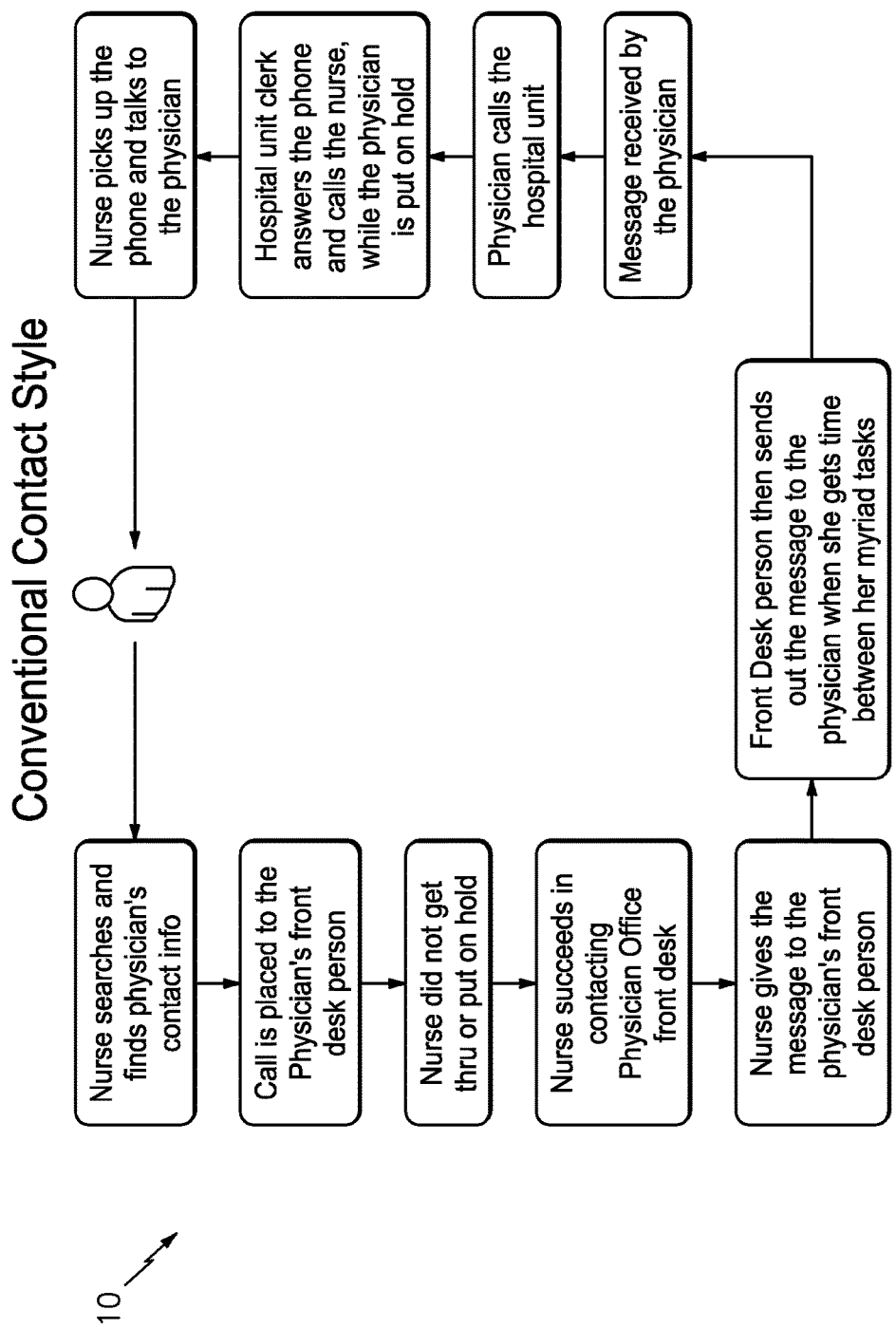
FIG. 1 is a simplistic block diagram illustrating a contact cycle, in accordance with the background art.

While the specification concludes with claims defining the features of the invention that are regarded as novel, it is believed that the invention will be better understood from a consideration of the description in conjunction with the drawings. As required, detailed embodiments of the present invention are disclosed herein; however, it is to be understood that the disclosed embodiments are merely exemplary of the invention which can be embodied in various forms. Therefore, specific structural and functional details disclosed herein are not to be interpreted as limiting, but merely as a basis for the claims and as a representative basis for teaching one skilled in the art to variously employ the inventive arrangements in virtually any appropriately detailed structure. Further, the terms and phrases used herein are not intended to be limiting but rather to provide an understandable description of the invention.

Identical reference numerals are used for like elements of the invention or elements of like function. For the sake of clarity, only those reference numerals are shown in the individual figures which are necessary for the description of the respective figure.

Although described throughout this document as directed to the health care industry, the inventive concepts disclosed herein are equally applicable to any number of different industries such as education, legal, manufacturing, and/or general business, for example.

Definitions.

As described throughout this document, the term "medical professional" and "Physician" shall be utilized to describe health care professionals which are employed by a doctor office. The term "doctor office" shall refer to the physician's independent practice group that provides medical professionals to care for patients at medical facilities.

The term "facility", "health care facility" and "medical facility" can be used interchangeably to refer to a location wherein patients receive medical services. Several non-limiting examples include hospitals, outpatient surgical centers, pharmacies, and the like.

The term "facility employee" can refer to any person employed at or by the medical facility, and who desires to communicate patient information with a Physician. In various embodiments, the facility employee may also be medical professionals such as a medical doctor, clinician, nurse, physician's assistant, and/or nurse practitioner, for example.

The term "patient information" can include any information which is desirable to send between a Physician and a facility employee. This patient information can be sent as either a voice or data communication, and can include, for example, patient reports, diagnosis, test results, room information, scheduling, and the like.

The term "Site Owner" can include an individual or legal entity that is providing, hosting, and/or facilitating the platform, and/or method steps disclosed herein. In one preferred example, the Site Owner will be a duly organized company utilizing the name VConnectMD and having a website that utilizes the same name. Of course, this is for illustrative purposes only, as the general platform, including any and all method steps and/or systems can be performed on any number of different websites and/or computer networks, and under any number of different names. Finally, the term "audio/visual communication" is inclusive of audio only communication, visual only communication, and a combination of audio and visual communication.

The below described system and method can function to standardize contact processes via a single portal. Based on the "On Call" schedule, the platform can display the "Covering Person(s)" for the person(s) selected by the sender or caller. For example, in a health care setting, the physician's contact information, contact preference, forwarding options, call routing preferences, and call schedule are assembled and maintained in the application. With this information, the platform can automatically display the "covering person(s)" for the selected person(s), highlight, and automatically check the person's name based on a unique call routing algorithm so that a secured message is sent to the correct person at the correct time by the preferred delivery method along with any attachments if required. The sender can also have an option to contact the pertinent person by secured text messaging or direct phone call. The phone number of the receiver is not revealed to the sender. Alternatively, the caller can have an option to make an online audio or video call based on receiver presence.

With specific respect to the health care industry, the platform can function to ensure that patient information is delivered to the correct person at the correct time using the correct delivery method across various participating entities based on receiver and entity preferences, several examples of which are described below.

As will be appreciated by one skilled in the art, aspects of the present invention may be embodied as a system, method, and/or computer program product. Accordingly, aspects of the present invention may take the form of an entirely hardware embodiment, or an embodiment combining software and hardware aspects that may all generally be referred to herein as a "circuit," "module," "system", or "feature." Furthermore, aspects of the present invention may take the form of a computer program product embodied in one or more computer readable medium(s) having computer readable program code embodied thereon, while other aspects may utilize traditional mechanisms for conducting voice communications. In either instance, the system and other computer hardware will be necessary to facilitate the communication of patient information between care providers.

Figure 2:
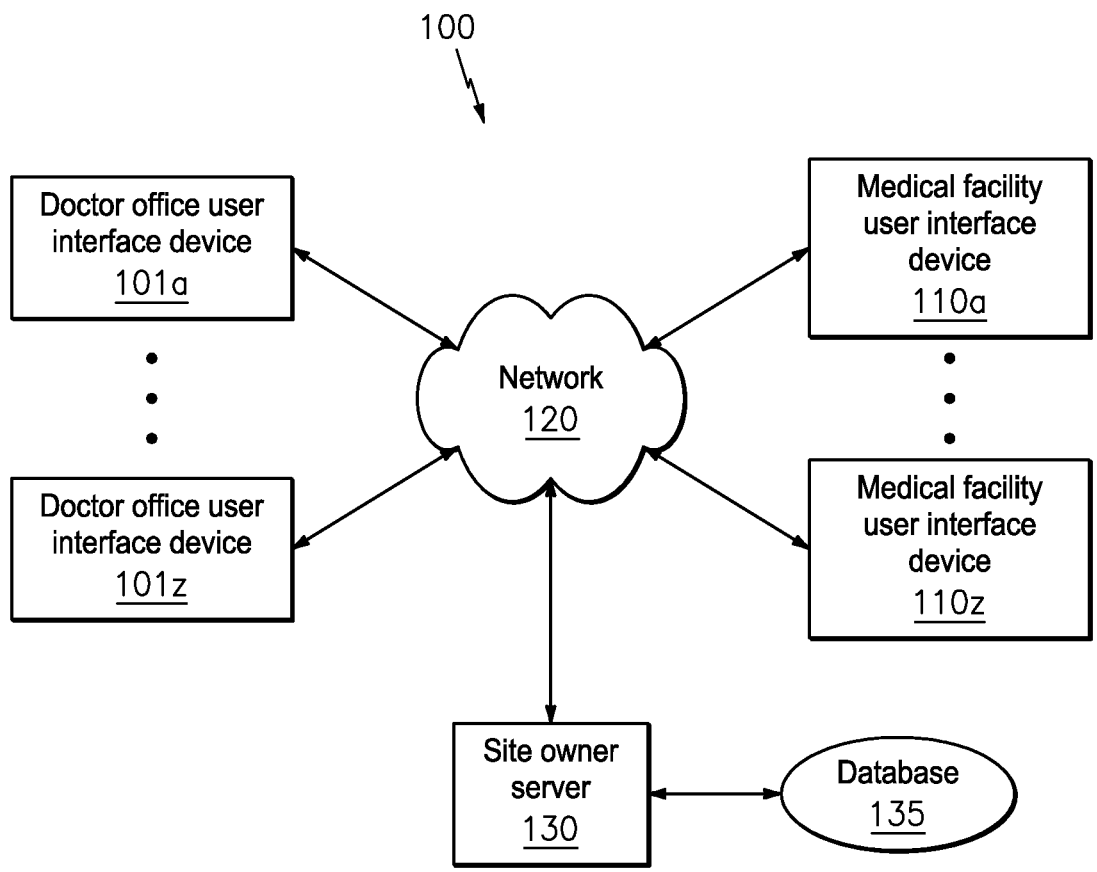
FIG. 2 shows an exemplary network environment according to one embodiments of the technology.

FIG. 2 is a schematic illustration of an exemplary system operating environment 100 for implementing the below described automated contact and information delivery method. The system 100 can include, for example, one or more user interface devices 101a-101z, which can be located at a doctor's office, for example, and one or more facility interface devices 110a-110z, which can be located at a medical facility such as a hospital or surgical center, for example. The interfaces can be connected over a network 120 to a site owner system 130 hosting various features of the below described methodology.

Although illustrated with respect to a single doctor office, and hospital, this is for ease of illustration, as the system is designed to facilitate communication between multiple health care providers and facility locations such as doctor offices, hospitals, outpatient surgical centers, pharmacies, and the like.

The site owner system 130, according to one embodiment, can include one or more individual computing devices that can be connected to one or more databases 135 on which various portions of the method can be performed. The system 130 can function to provide a central hub for controlling the communication between the various user interfaces 101 and 110, through any number of different mediums such as the above noted website, for example. In this regard, one or more of the individual computing devices described herein as the owner system can comprise a web server, an email server, a communication server, and so forth, or the system can employ a single server device which functions to handle each of these processes.

Portions of the below described method can be implemented as a computer program product, i.e., a computer program tangibly embodied in a non-transient machine-readable storage device, for execution by, or to control the operation of, a data processing apparatus. The computer program can be written in any form of computer or programming language, including source code, compiled code, interpreted code, scripting code (e.g., JavaScript) and/or machine code, and the computer program can be deployed in any form, including as a stand-alone program or as a subroutine, element, or other unit suitable for use in a computing environment.

The database 135 can include one or more independent storage devices that can function to receive and store any form of information. In one embodiment, the database can function to receive and store provider and/or patient information. As described herein, the database 135 can include various types of computer-readable storage mediums, such as, for example, semiconductor memory devices, e.g., DRAM, SRAM, EPROM, EEPROM, and flash memory devices; magnetic disks, e.g., internal hard disks or removable disks; magneto-optical disks; and optical disks, e.g., CD, DVD, HD-DVD, and Blu-ray disks. In addition, the devices can be operatively coupled to a communications network, such as network 120, to receive instructions and/or data from the network and/or to transfer instructions and/or data to the network.

Each of the interface devices 101 and 110 can include processor-enabled devices such as a computer, tablet, or smart phone, for example, that can be operated by a human user. Moreover, each of the interface devices can also include one or more client applications, such as a web browser, for example, which can allow the device user to communicate with and view content from other devices over the network 120. Owing to the sensitive nature of the information to be shared across the system, and in order to be HIPAA compliant, each system component 101, 110, 130 and 135 can preferably be constructed utilizing purpose-built interface devices having dedicated and password protected internal or external storage mediums. These purpose-built devices can further include network interface devices having an embedded random number generator which can be synced across each system device. Such a feature can allow the purpose-built non-generic processor enabled devices to perform the below described methodology in a completely secure manner that cannot be achieved through the use of off-the-shelf hardware.

In various embodiments, the network 120 is a transmission medium that facilitates any form or medium or digital or analog communication (e.g., a communication network). Transmission mediums can include one or more packet-based networks and/or one or more circuit-based networks in any configuration. Packet-based networks can include, for example, the Internet, a carrier internet protocol (IP) network (e.g., local area network (LAN), and/or a wide area network (WAN). Circuit-based networks can include, for example, the public switched telephone network (PSTN), a wireless network (e.g., RAN, code-division multiple access (CDMA) network, time division multiple access (TDMA) network, global system for mobile communications (GSM) network), infrared transmissions, Blue Tooth or Personal Area Networks (PANs), Near Frequency Communication (NFC) network, and/or other circuit-based networks.

Information transfer over the network 120 can be performed by a communication module based on one or more communication protocols. Communication protocols can include, for example, Ethernet protocol, Internet Protocol (IP), Voice over IP (VOIP), a Peer-to-Peer (P2P) protocol, Hypertext Transfer Protocol (HTTP), Session Initiation Protocol (SIP), a Global System for Mobile Communications (GSM) protocol, a Push-to-Talk (PTT) protocol, a PTT over Cellular (POC) protocol, a Real-time Messaging protocol (RTMP), a Real-time Media Flow Protocol (RTMFP) and/or other communication protocols.

A method for performing automated contact and information delivery can function to allow secure and auditable communication across facilities such as hospitals and surgical centers, for example, and the care providers such as doctors and doctor offices, for example that utilize the same. In essence, the system and method allow facility employees, such as nurses to quickly identify and contact a physician (or other person designated by the physician) that is overseeing a patient located at the facility.

Because it is common within the medical community for one physician to cover another physician's patients, the method includes functionality for allowing a doctor's office to dictate where a communication is sent, based on several factors, such as the physicians availability and/or the seriousness of the request. For example, if the message from the facility is routine and the physician is home for the day, the system can hold delivery of the message until the next morning, or other such time that is pre-selected by the physician. Conversely, if the message pertains to an urgent situation, system method can automatically connect the facility to the physician's cellular telephone, home phone, or other location designated by the physician and/or any other individuals selected by the physician.

A method for performing automated contact and information delivery utilizing the network system 100 will now be described with respect to FIG. 3. Moreover, several exemplary presentation screens which can be generated by the system are presented with respect to FIGS. 4A-7. Although described below with respect to particular steps and screens, this is for illustrative purposes only, as the methodology described herein can be performed in a different order than shown, and the presentation screens can include any number of additional information and features.

Figure 3:
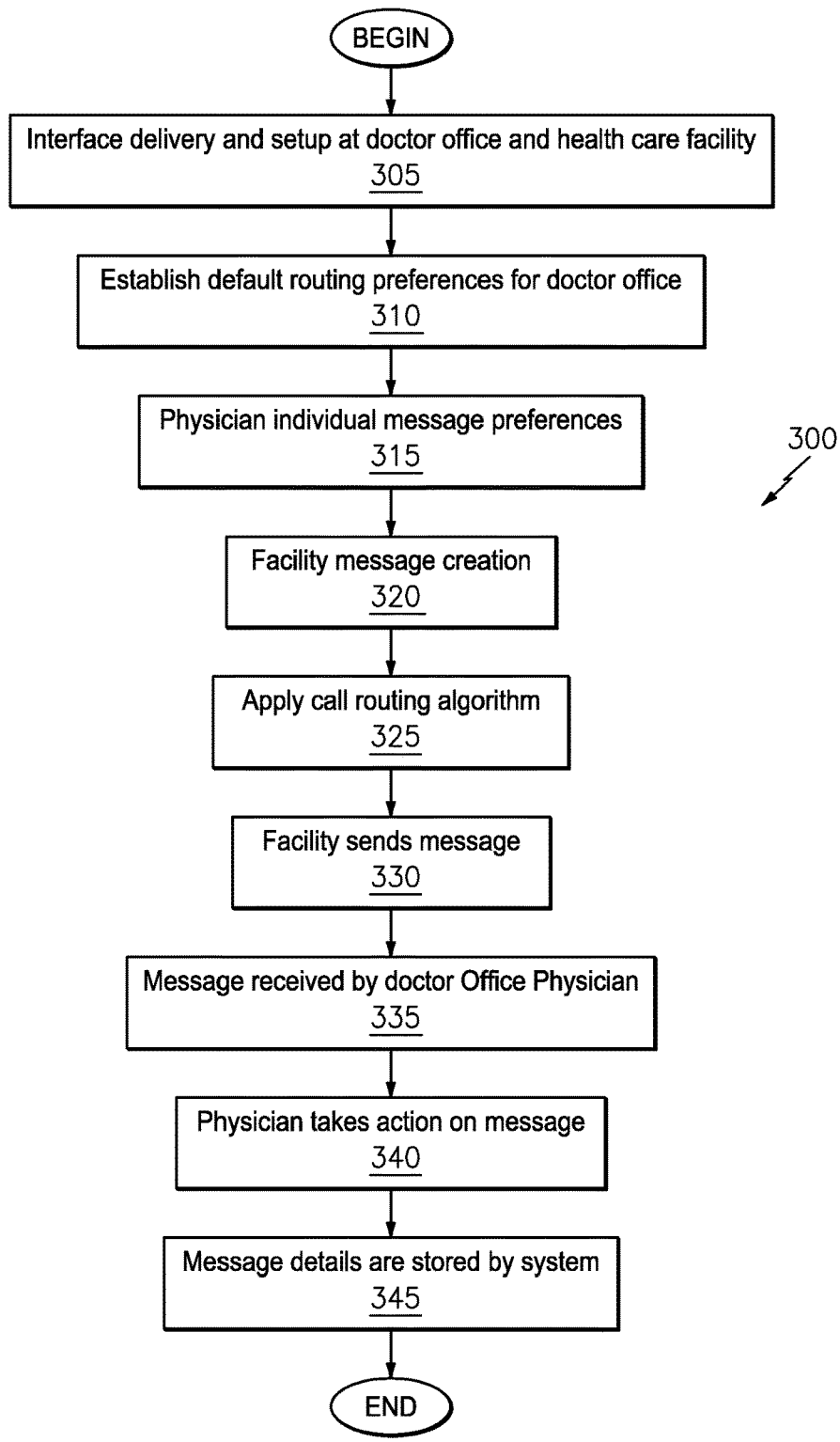
FIG. 3 shows an exemplary flow diagram illustrating a method for performing automated contact and delivery of patient information, in accordance with one embodiment.

FIG. 3 illustrates an exemplary flow chart method 300. The method begins at step 305 with the installation of one or more user interface devices at any number of different healthcare facilities and doctor offices. The installation procedure includes connecting each of the user interface devices to the site owner server over a network, and ensuring each device can communicate in a secure manner.

Once the installation procedure has completed, the method can proceed to step 310, wherein a system administrator from each doctor's office can setup default settings pertaining to how messages and calls from facility employees are routed to the physicians (referred to hereinafter as call routing). This information can be collected via a call routing module.

FIG. 4A is an exemplary call routing page 400, which can be generated by the call routing module of the site owner 130 to be displayed on one or more of the doctor office interface devices 101. As shown, the page 400 can allow the doctor office administrator and/or a health care facility administrator to establish how calls and messages are routed, when utilizing the below described Connect on Call module.

In the present example, these options will pertain to a cardiologist doctor's office 401 that provides cardiologists, physicians and other medical professionals to health care facilities. To this end, the system administrator can identify one or more of the offices' medical professionals 405 to whom a call should be routed based on several different factors. As shown, the factors can include, but are not limited to the selection of a call from location 403, the selection of a call reason 404 and the selection of a call type 402 on the call routing presentation screen 400.

In addition to the above, the administrator can establish default and override settings that account for virtually every situation encountered by the medical professionals at the health care facility. To this end, because the most common form of messaging will pertain to routine patient care messages, the default call information setting 406 is provided as shown. The default call information 406 pertains to a situation in which call information screens 602, 603 and 604 of the below described connect on call module are pre-selected. As shown, in these instances, the medical professionals identified to receive such messages will be either the day call nurse practitioner and/or physician assistant.

However, in instances where the message pertains to a potentially serious situation such as CT &CF (i.e., cath and/or stemi) 407, or CT 409, the system can automatically identify a physician as the medical professional to whom the call should be routed. As noted above, the call routing logic imparted by the system can include a vast array of options based upon different parameters of the medical facility and the doctor office.

As will be obvious to those of skill in the art, the illustrated lists of "Types", "From", "Reason", and "Route" are exemplary in nature, so as to provide a clear understanding of the basic system concepts. In practice, the system will include several additional features, such as various overrides and/or additional categories. Such features providing users the ability to override default settings if called for by a particular situation. Moreover, although described as a "call" this also includes textual communication.

Figure 4B:
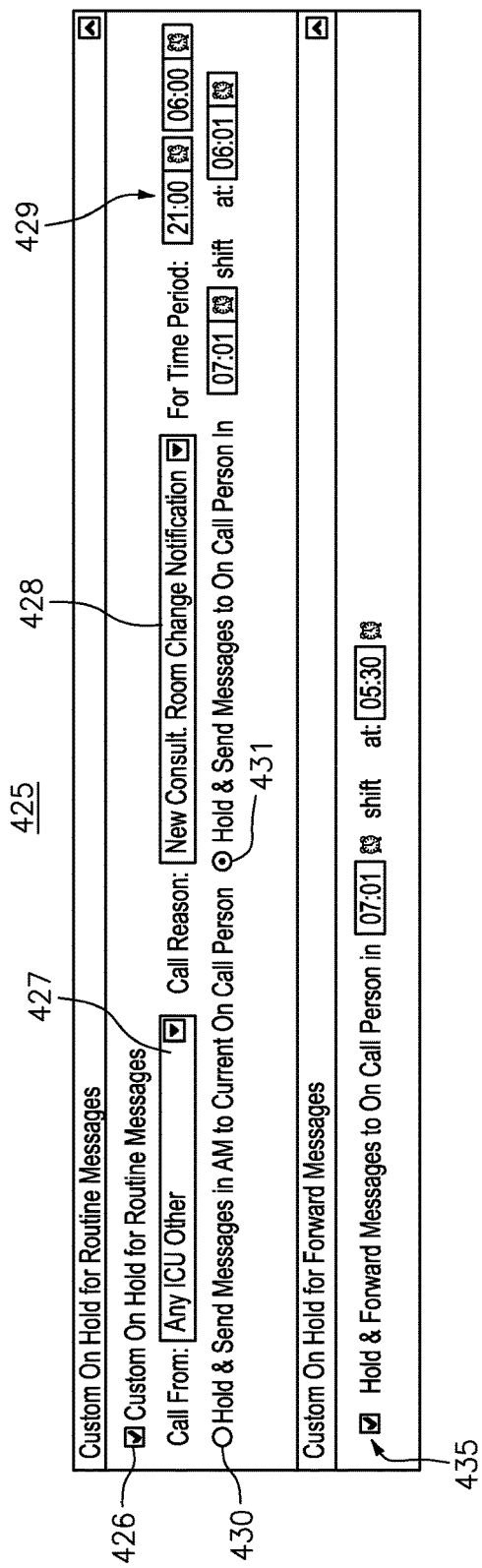
FIG. 4B shows another exemplary user interface of the system of FIG. 1.

Next, the administrator can establish the preferred mechanism for holding and or forwarding routine messages. To this end, FIG. 4B illustrates one example of a custom On Hold for routine messages module 425. As shown, this feature allows the system to hold 426 routine messages from certain groups 427 and for certain reasons 428 that are generated during a certain shift 429 (e.g. night shift 11 PM to 6 AM). The message(s) are to be held in queue and then sent in AM either to On Call Person in current shift 430 or to the On Call person in AM Shift 431, as per the below described call routing algorithm. The on hold messages are delivered to individual receiver's at a custom AM time set in their Profile. The Message delivery is defined by the Receiver's Call Group and Auto-initiated. Messages are forwarded to current on call person or the on call person(s) for another shift defined by the Call Group. The delivery time will be as per Receiver's preference. If the Receiver has not specified the time to receive on hold messages in his or her profile then the message is delivered as specified by the call group. If the Receiver specified time is earlier than that specified by the Call Group—then the message is sent to the Receiver as per the time specified by the call group.

Likewise, the system can also allow the user to select one or more messages and forward them 435 to one or more specified users of Self-Tenant, Affiliated Tenant or External Users at one shot. The External User list can be accessed from user's phone book or manually entered by the user. The user has an option to send the message now or in AM. If the Send in AM option is chosen, the Messages are held in queue and sent to the specified Receiver, based on the time to Receive On Hold Messages specified in his/her profile. If no time is specified then the message is delivered at the time specified by the Receiver's call group. For Forwarded Messages, if no time is specified by the Receiver's call group then the Message is delivered at 7 AM. For the On Call Messages the User also has an option to forward the Message to AM Shift On Call Person, without having to select a specific person. The system automatically sends the message to the covering person based on the routing logic customized to that Receiver's Call Group. The forwarded messages are marked as such for sender's knowledge. The messages that are held in queue are also marked as in queue for sender's knowledge. This way the sender can know from his/her message log itself, which messages are forwarded and which messages are in queue. The message cannot be forwarded outside the application to prevent data leakage.

Once the office defaults have been established, the method can proceed to step 315, wherein each medical professional of the doctor office can select their individual message routing and delivery preferences. Although not illustrated, one or more presentation screens can be provided that allow a medical professional to enter their contact telephone numbers such as Home, Office, Mobile, Fax, etc., along with email address and other such contact information. Additionally, the medical professional's work schedule days and hours can be input into the system. This can be performed utilizing any number of different methods such as importing from a calendar system, or manually selecting the days and hours. In either instance, once the system has been provided with the medical professional's contact details and working schedule, he or she can select preferences for how and when they are to be contacted.

Figure 5A:
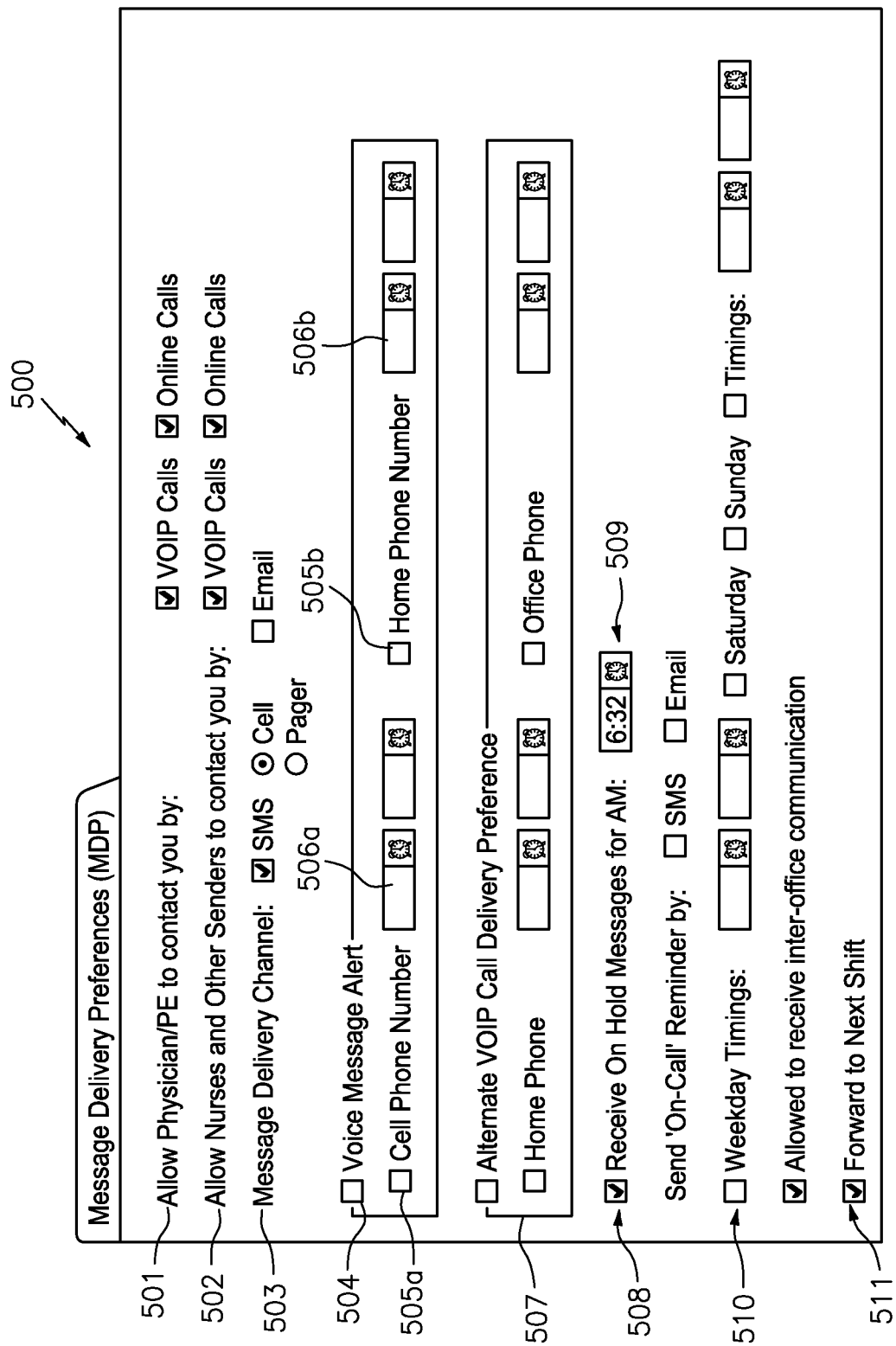
FIG. 5A shows another exemplary user interface of the system of FIG. 1.

To this end, FIG. 5A illustrates one example of a Message Delivery Preferences (MDP) page 500, which can be generated by the site owner 130 to be displayed on one or more of the doctor office interface devices 101. As shown, the MDP can allow medical professionals to select their preferred contact preferences. As will be described below in detail, the system can allow facility employees to directly call the identified medical professional without actually being provided the medical professional's private telephone number(s). To this end, physicians can input personal contact details such as their pager number, online telephone number, personal email address, home telephone number, office telephone number and/or cellular telephone numbers to the system and the system can route calls from medical facilities directly to the provided phone number(s). Such a feature advantageously provides a means for facility employees to reach a physician in a given circumstance without being given the personal contact details of the medical professional, thereby preventing misuse of the information.

To this end, the MDP provides physicians with multiple contact options based on communications from other Physicians 501 and/or nurses 502, as well as designating the delivery channel 503. The MDP also allows the physician to select if they wish to receive voice message alerts 504, and if so, the telephone number 505a-505b and/or times 506a-506b which the alerts can be sent. Physicians can also be presented with alternate VOIP call delivery preferences 507.

In addition to the above, the system can also include functionality for delaying message notifications referred to as Message Hold and Forward 508 based on the preference of the physician. To this end, Physicians can select the preferred time 509 which such messages will be received. Moreover, these delivery options can be adjusted based on the day of the week 510, and/or allow the system to automatically forward the message(s) to the next shift person 511. Such a feature allows messages to be delivered in a manner that is complementary to the physicians working schedule.

Figure 5B:
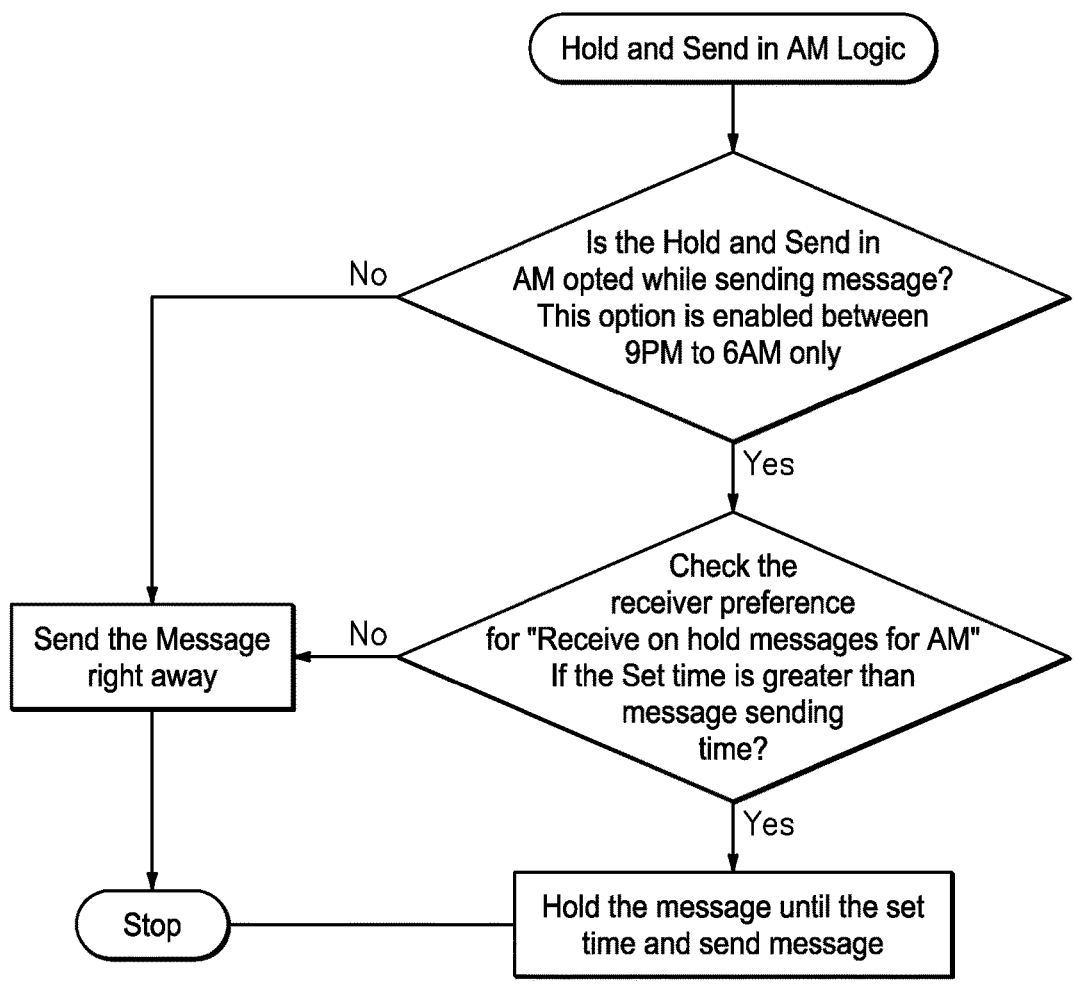
FIG. 5B shows an exemplary flow diagram illustrating steps for performing a message hold procedure of the contact and delivery method, in accordance with one embodiment.
Figure 5C:
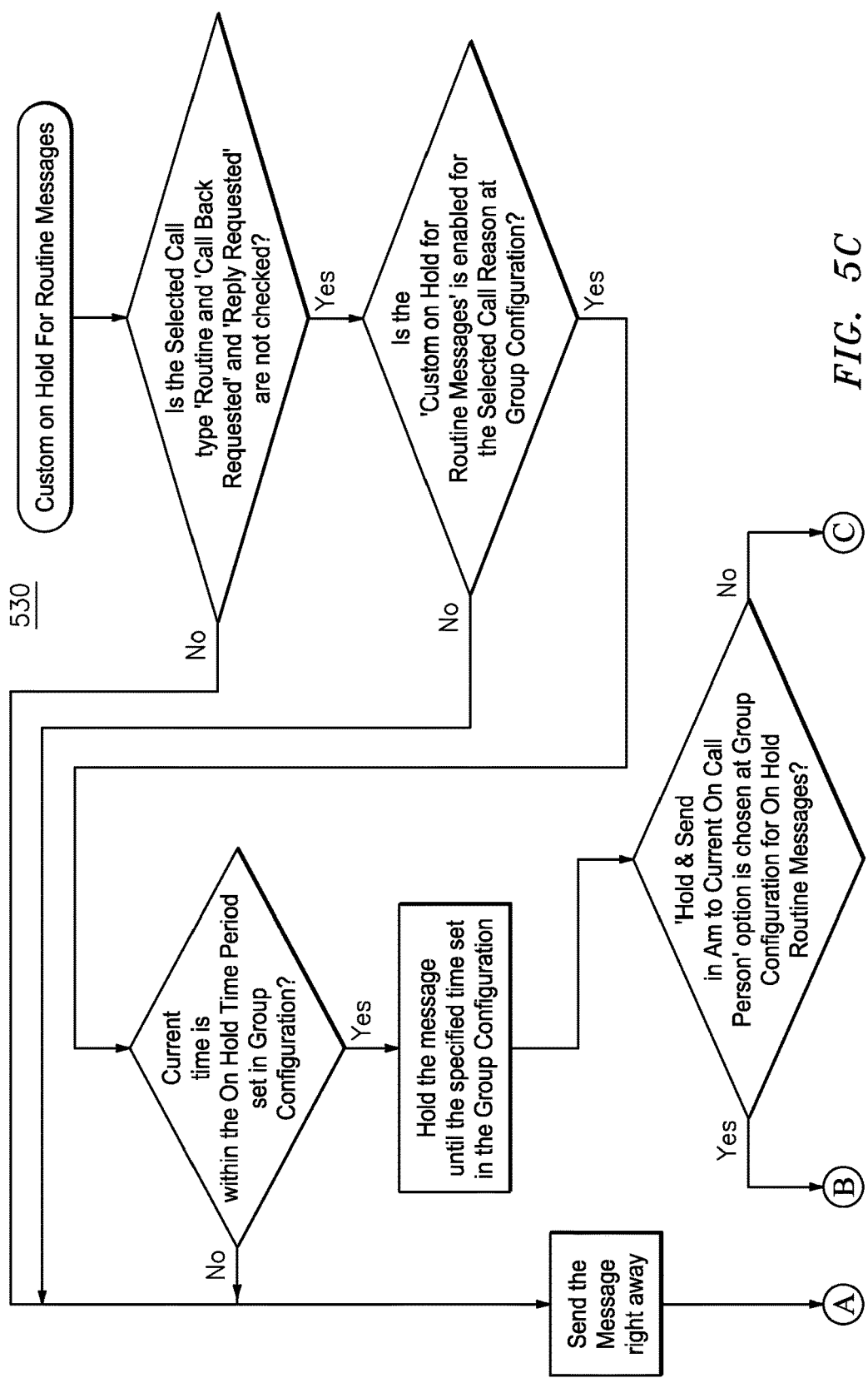
FIG. 5C shows an exemplary flow diagram illustrating steps for performing a custom message hold procedure of the contact and delivery method, in accordance with one embodiment.
Figure 5C:
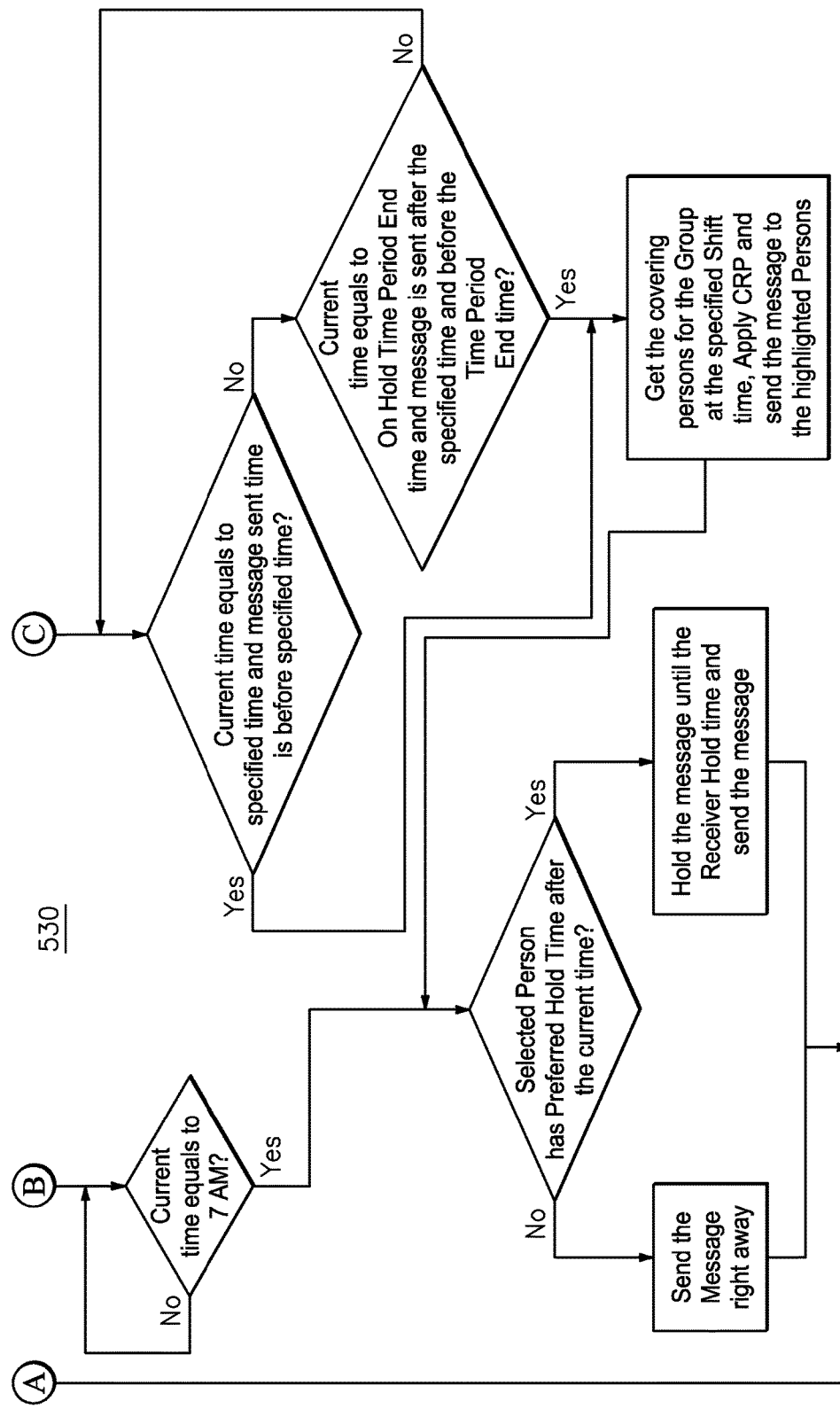

FIG. 5B is a flowchart illustrating an exemplary method 525 which can be performed by the system, when the On Hold message settings 508 are active. Likewise, FIG. 5C is a flowchart illustrating an exemplary method 530 which can be performed by the system to include the user custom features identified above with respect to option(s) 510. As shown, the physician can be provided with the option to forward a message securely to the next shift person. When the next shift person option is selected a message is automatically routed to the next shift person based on call location, call schedule, call type, call from and call reason of the original message. The receiver will receive the message based on his/her selected time for on hold messages. The receiver's call group has an option to specify the shift and delivery time of such messages. This way the sender does not have to wait till the beginning of the next shift to forward a message to the next shift person. Once a message is received and acted upon by the Receiver, the Receiver can in turn forward the message for further action to the next shift person with in his/her call group at any time and the message is held in queue and automatically sent to the right person at a specified time. Also the Sender does not have to know which particular person the message needs to be forwarded, since based on patient location, call schedule, call type, call reason and call from values contained within the message, the system selects the pertinent next shift person and sends it automatically.

The forwarded messages are marked as such for sender's knowledge. The messages that are held in queue are also marked as in queue for sender's knowledge. This way the sender can know from his/her message log itself, which messages are forwarded and which messages are in queue. The message cannot be forwarded outside the application to prevent data leakage.

Figure 5D:
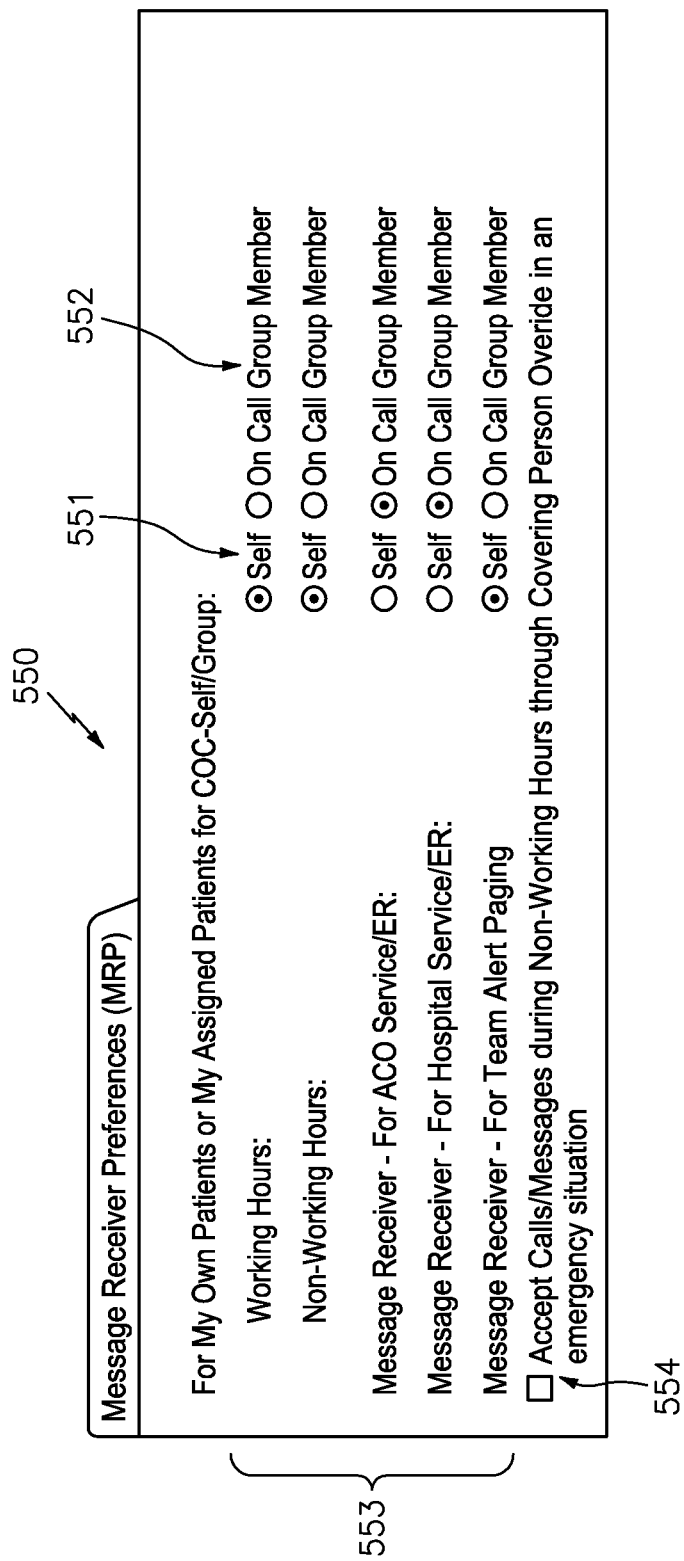
FIG. 5D shows another exemplary user interface of the system of FIG. 1.

In addition to the above, FIG. 5D illustrates one example of a Message Receiver Preferences (MRP) page 550, which can be generated by the site owner 130 to be displayed on one or more of the doctor office interface devices 101. As shown, the MRP can allow physicians to designate whether they should receive a message 551, or if it should be delivered to a covering physician 552, based on several different factors 553. Moreover, the physician can be provided with an override setting 554 to be contacted if the message involves a patient experiencing an emergency situation.

Of course, the above noted presentation screens 500 and 550 are intended to be exemplary in nature, so as to provide an understanding of the basic system concepts. In practice, the above noted screens can include several additional and/or different features, pertaining to message receiver and delivery preferences.

Now that the doctor office defaults 400 and individual physician message preferences 500-550 are established, the method can proceed to step 320, wherein a facility employee can utilize the system to communicate patient information with a physician via the Connect On Call module of the system. Although illustrated with respect to communication from a facility employee to a physician, this is for illustrative purposes only, as virtually any system user can communicate with another system user by following the same basic steps.

Figure 6A:
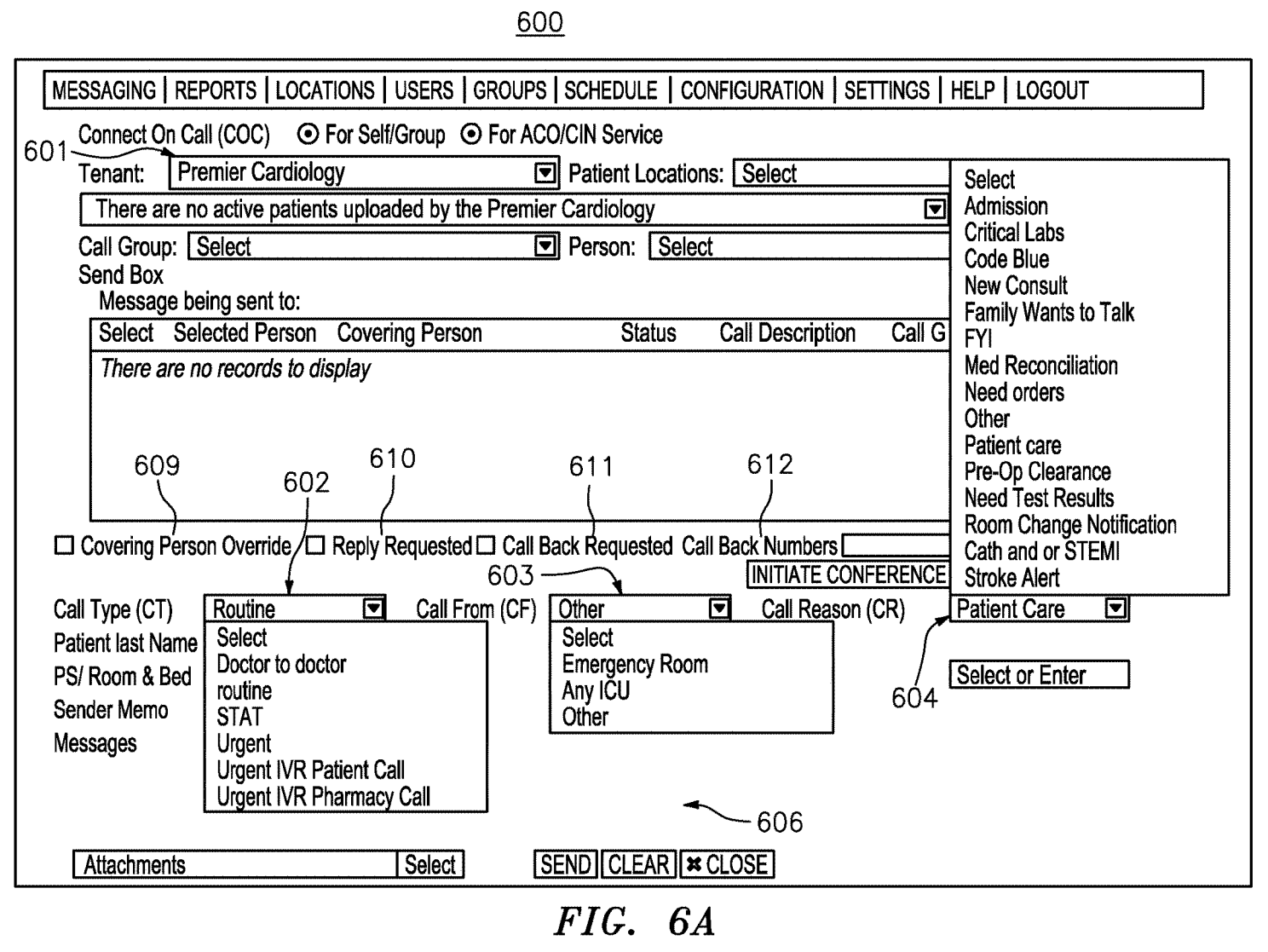

FIG. 6A is an exemplary screenshot of the Connect On Call (COC) module 600, which can be generated by the site owner 130 to be displayed on one or more of the doctor office interface devices 101 and/or facility user interface devices 110. In the present example, the message is being displayed on a facility user interface by a nurse attempting to communicate patient information to a physician.

As shown, the page 600 can allow the nurse or other facility employee to identify and contact any number of different physicians who are overseeing the care of a patient. In the illustrated example, the message pertains to cardiac care, so the tenant 601, selected by the nurse is the Doctor Office Premiere Cardiology, described above with respect to FIG. 4A at 401. As shown, once the doctor office has been selected, the call information options 402, 403 and 404 will be pre-selected to display the default call information settings 402, 403 and 404 described above at 406. At this time, the nurse can adjust one or more of the call information options based on the current situation. To this end, the nurse can adjust one or more of the type of call 602 e.g., routine, STAT, Urgent, Doctor to Doctor . . . , who the call is from 603, e.g., the nurses department at the medical facility, and the reason for the call 604.

As each of the call information options 602-604 correlate directly to options 402-404 displayed in FIG. 4A, changing one of the options will change who the system identifies as the correct medical professional 605 to contact. In various instances, the system can provide the nurse with additional options, such as to override the identified medical professional 609, request a return message 610, and/or a return call 611 at a designated phone number 612.

In either instance, once the nurse has selected options 602-604, the method can proceed to step 325, wherein the system can apply the selected options to a call routing algorithm that can identify the correct medical professional 605 from the doctor's office based on the unique factors of the patient, the location, the reason for the message, and the Doctor Office settings. In this regard, the call routing algorithm can include several factors such as, for example: Message Delivery Preferences (MDP): Messages to be delivered only to Application Inbox or also as SMS, Email, or to Pager and Message Alerts to be delivered as SMS, Email, or to Pager); Call Routing Preferences (CRP)—That is determined by call type, call reason and call location selected by the sender. The message to be received by self or other on call members based on these values; Workflow Rotation Preferences (WRP): based on call reason {e.g. consults & admissions} selected by the sender); Work Assignment (WA): Patient's Assigned Physician for a given work shift; On Hold Message Preference (HM): Certain routine messages sent during night shift to be held in queue and sent to covering person in AM Shift; Person Assignment (PA): Message to be received by self or on call group member; and/or On Call Schedule (OCS): Which shows who is on call for a given time shift and date.

Figure 6B:
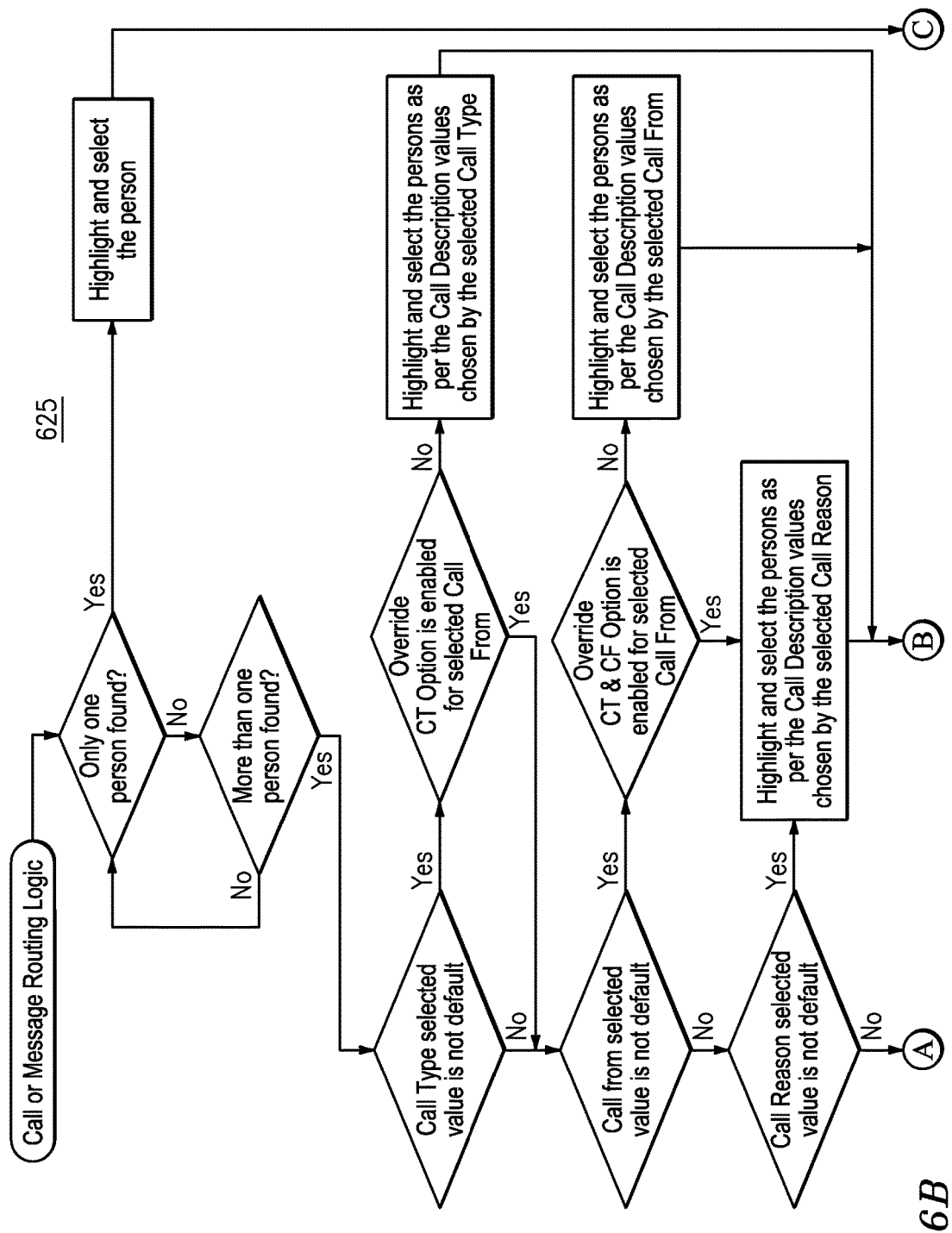
FIG. 6B shows an exemplary flow diagram illustrating steps for performing the call message routing feature of the contact and delivery method, in accordance with one embodiment.
Figure 6B:
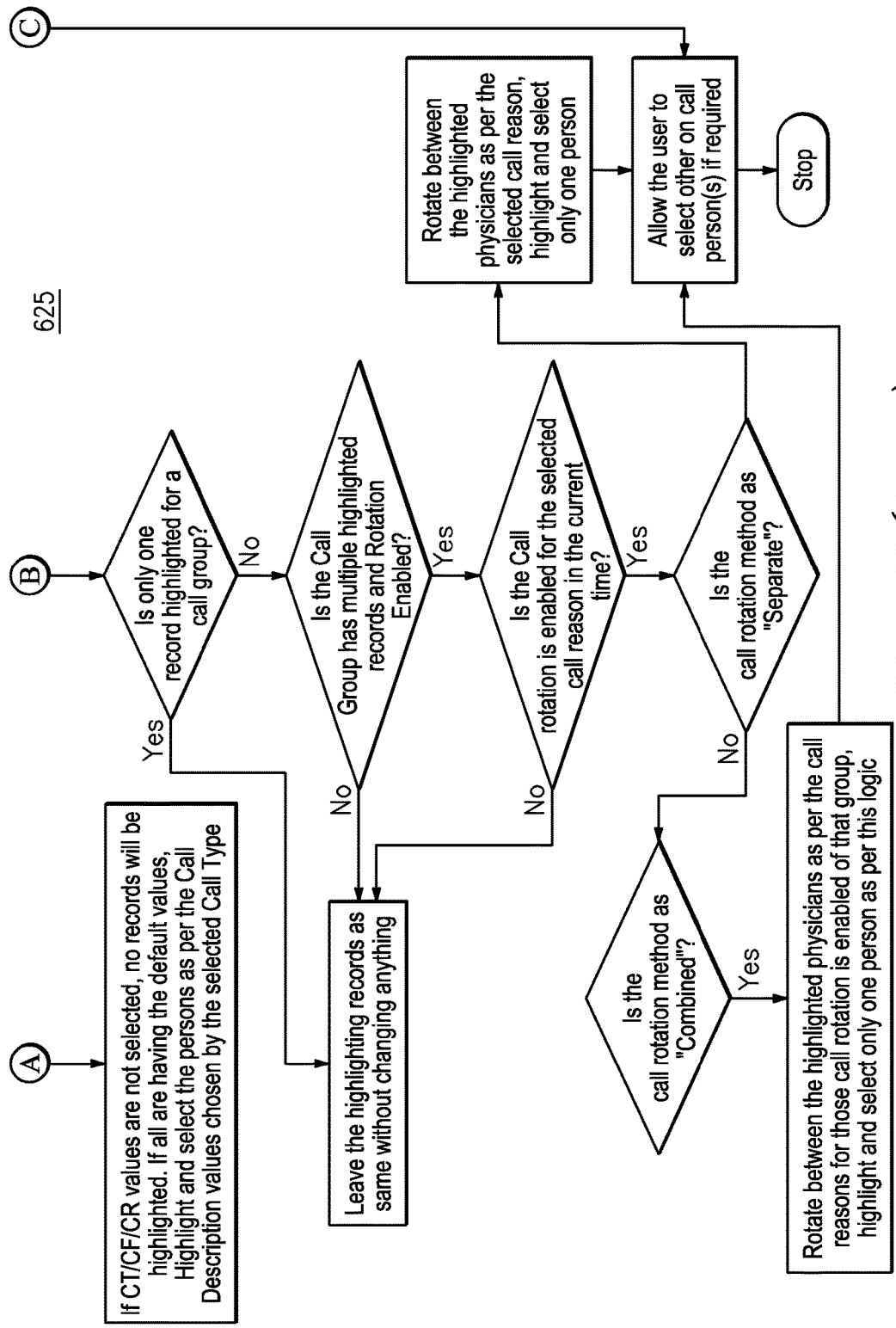

Accordingly, FIG. 6B is an exemplary flowchart illustrating one possible routing algorithm 625 which can be performed by the system, based on the factors described above. As shown, based on the On Call Schedule, the application can display the Covering Person(s) for the Physician(s) selected by the facility employee. Based on Call Routing Preferences (that is in turn based on Call Type, Call Reason and Call Location selected by the Sender), Work Flow Rotation Preferences, Work Assignment and Person Assignment Preferences of the Receiver the application then auto highlights and auto checks the covering person(s) to indicate the Receiver preference of to whom the message or call should be routed to. The User has the option to send the message to the medical professional(s) selected by the system or select an alternate covering person available or even choose the selected person even though that person is not on call at that time but available.

Figure 6C:
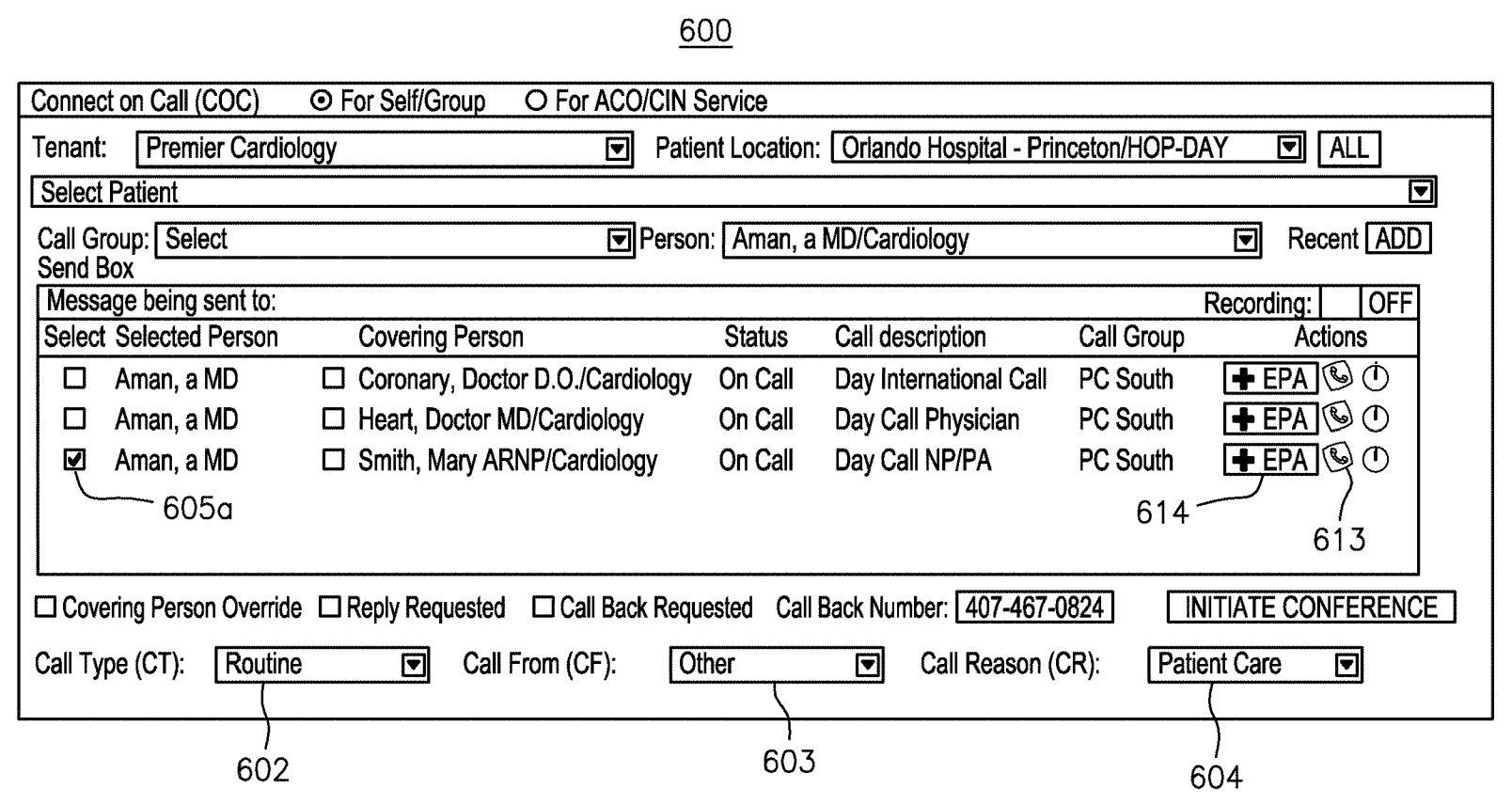

As shown in FIG. 6C, if the facility nurse selects the call type 602 as "routine" the call from 603 as "other" and the call reason 604 as "patient care", the system can automatically identify and display the day call Nurse Practitioner 605a as the correct medical professional to receive the message. Conversely, as shown in FIG. 6D, if the matter is urgent, and the facility nurse selects the call type 602 as "STAT" the call from 603 as "ICU (intensive care unit)" and the call reason 604 as "critical", the system can automatically identify and display the day call Physician 605b as the correct medical professional to receive the message.

In either instance, once the correct Doctor Office physician/employee has been identified as described above, the facility nurse can then enter the message details into a text box 606 (i.e., textual communication) and may add any attachments 607 such as medical records, for example, before sending 608 the message to the physician. Moreover, if the nurse would like to physically speak with the identified doctor office physician (i.e., audio/visual communication), the facility nurse can select option 613 which can initiate a VOIP call, including voice and/or video, between the user nurse's user interface and the physician. To this end, the VOIP system will contact the physician or their covering person, based on the message delivery preferences (MDP) and/or message receiver preferences (MRP) identified by the physician at step 315, and at presentation screens 500 and 550.

In addition to the above, should the nurse select any options involving the above described CT &CF, or CT, the system will automatically change the identified medical professional 605 based on the override procedures described with respect to FIG. 4A. Moreover, the system can provide one or more options for allowing the nurse to immediately contact the identified medical professional 605 in an emergency situation. To this end, if a nurse selects the Emergency Person Access 614 (EPA), the system can immediately contact the nurse to the doctor as specified by the doctors MDP and MRP settings, and/or provide the actual contact details to the nurse.

Figure 6E:
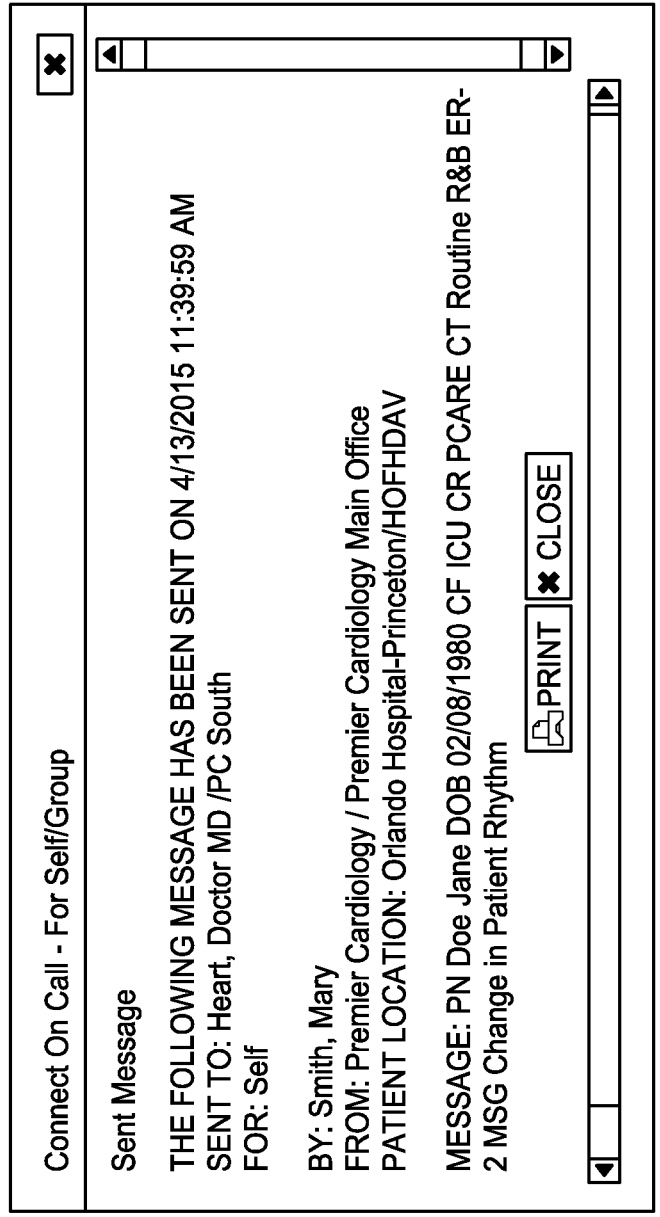
FIG. 6E shows another exemplary user interface of the system of FIG. 1.

Returning to the example, upon inputting a message into the text box 606, the method can proceed to step 330, wherein the message can be sent to the physician. Upon sending the message, the nurse is provided with a confirmation of the message 650, as shown in FIG. 6E. This confirmation can be printed or stored by the system in the communication log, thereby ensuring HIPAA compliance.

Next, the method can proceed to step 335 wherein the message is delivered to the physician in accordance with their specified MDP and MRP settings. To this end, routine messages can be routed to the Physician's inbox, and a notification of the message can be sent to the doctor immediately, or at a later time based on the physician's On Hold message settings 508.

Figure 7:
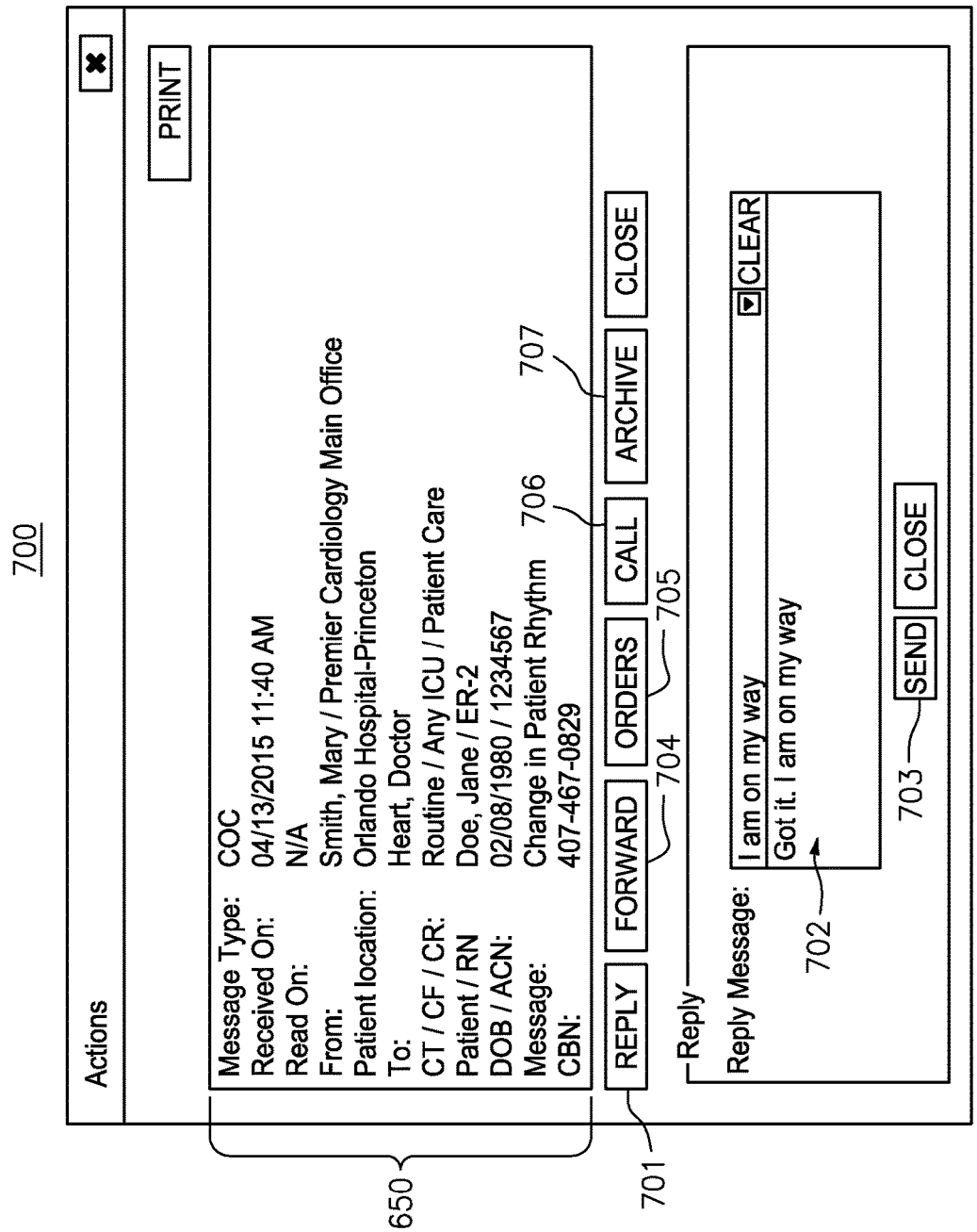
FIG. 7 shows another exemplary user interface of the system of FIG. 1.

Upon delivery of the message, the method can proceed to step 340, wherein the message is displayed to the Physician. To this end, FIG. 7 illustrates an exemplary message presentation screen 700 containing the original message 650. A non-exclusive list of options available to the physician can include a reply 701, wherein a text box 702 is created to allow the physician to type a response and send 703 the same back to the nurse. Additionally, the physician can forward 704 the message to another physician, such as the physician who is on the next shift, for example. The physician can also write new medical orders 705 such as lab tests, for example, call the nurse 706, and/or save the message in the physician's archive 707.

In this regard, the connect on call feature of the system allows a facility employee to identify, talk and/or send secure patient information directly to the proper physician at a doctor office, without having to know in advance who the doctor is, or their working schedule. Moreover, the contact details for the selected physician are not shown to the nurse, thereby preventing misuse of the same.

Upon acting upon the message, the method can conclude at step 345 wherein the message details, including any attachments, orders, and other such information can be stored within the system database(s) 135. This can be performed irrespective of delivery channels (emails, SMS, audio, video, and chat). To this end, the platform can permanently store the same along with a date and time stamp.

By permanently storing the messages, as described above, it becomes possible for managers to audit communications by searching messages utilizing any number of search filters, thereby reviewing all messages or calls with text, audio and video content. The unread messages and read messages are indicated clearly.

As noted above, it is important that all communications involving patient information be fully HIPAA compliant. As such, Messages sent via the platform are fully SSL/AES encrypted at rest and in motion. Each message inbox can be password and PIN-number protected, and the system can prevent messages from being forwarded outside of the application to prevent data leakage.

Figure 8:
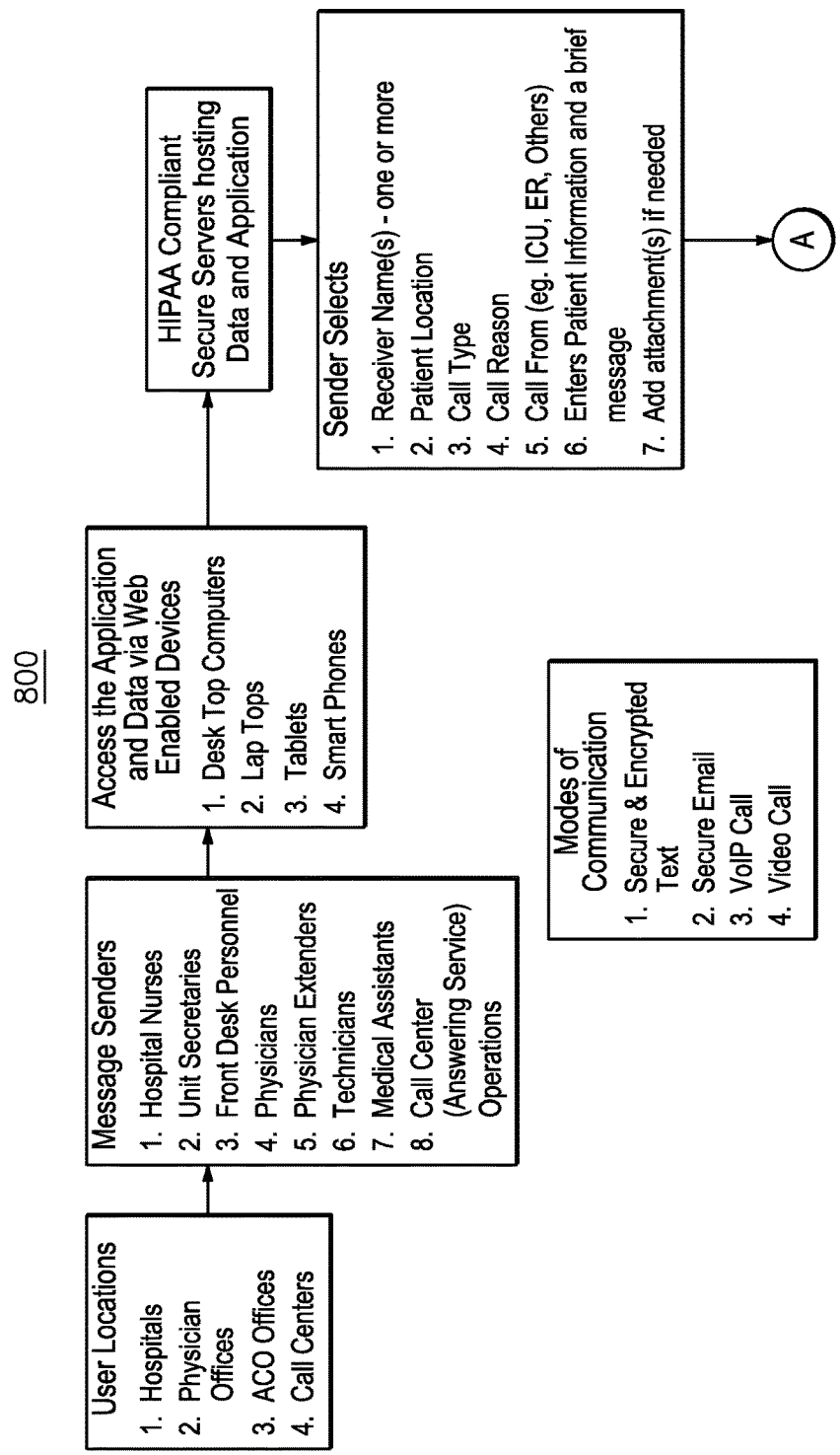
FIG. 8 shows an exemplary flow diagram illustrating the system methodology described above with respect to FIGS. 2-7.
Figure 8:
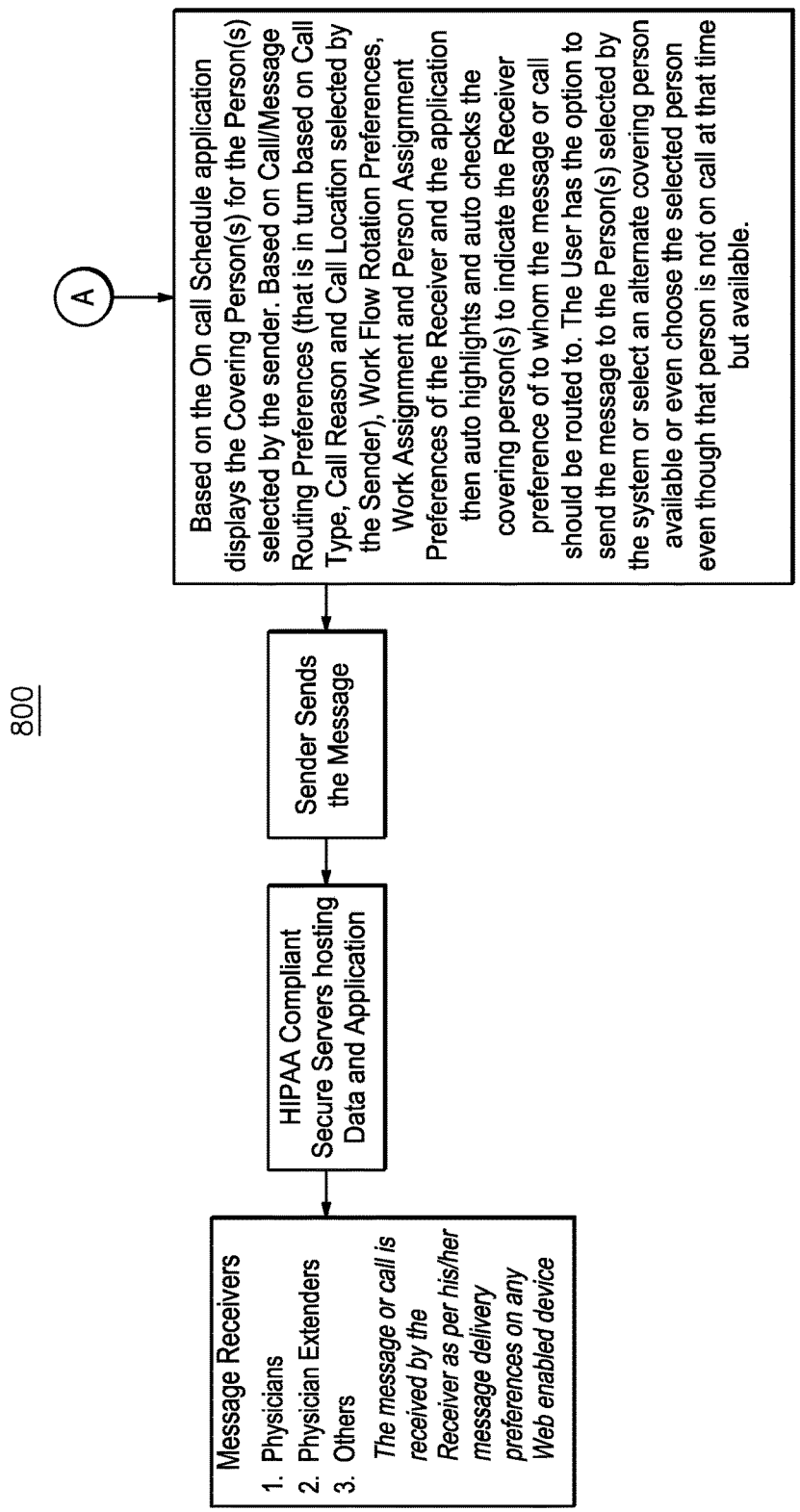

As summarized in the flowchart 800 of FIG. 8, the above described system includes functionality for providing multiple forms of communication across several different platforms and between various groups of medical professionals. The methodology employed by the system allows medical facility employees to immediately identify and contact physicians and other doctor office employees, and to securely deliver patient information.

Several types of audiovisual contact mechanisms which can be employed by the system include, but are not limited to: Direct VOIP Call: In emergency situations, a user can call a specific person without revealing the receiver's phone number to the caller. Online Audio Call: A user can make an online audio call to a specific person based on the presence, provided the caller has such a privilege granted and the receiver has given access to such a caller type. Online Video Call: A user can make an online video call to a specific person based on the presence, provided the caller has such a privilege granted and the receiver has given access to such a caller type. Online Chat: A user can start a chat session with a specific person based on the presence. Conference Call: The user (e.g. a nurse) can set up a conference call between different on-call physicians regarding the care of a critically ill patient if required.

Record Voice Conversations: The user initiating a phone call through the application can record the conversation. The voice file can be permanently stored in a message log. This log of all voice files can be kept for future access and review. The access to record voice conversation can be based on if the user was granted privilege to that feature or not. The receiver can be notified at the start of the call that the call is being recorded for documentation and quality purpose.

Multi Person Paging: This feature of the platform allows the user to send a common message simultaneously to the multiple selected physicians and others. The message can be routed to the pertinent covering persons automatically. This way, the Sender does not have to send the common message individually, saving valuable time while caring for a critically ill patient.

Automatic Reminders: Personal Messages and Group Messages can be sent to the receivers with sender preferred reminders about event descriptions and event dates and times. For example, a hospital medical records department person can send out messages to physicians regarding pending record completion with automatic reminders or a hospital chief of staff or other executives can send group messages to target audience regarding an important meeting or deadline with automatic reminders.

Accordingly, a system and method for performing automated contact and information delivery is disclosed herein. As to a further description of the manner and use of the present invention, the same should be apparent from the above description. Accordingly, no further discussion relating to the manner of usage and operation will be provided.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As will be appreciated by one skilled in the art, aspects of the present invention may be embodied as a system, method or computer program product. Accordingly, aspects of the present invention may take the form of an entirely hardware embodiment, or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Although described above as utilizing specific components, features and/or method steps, those of skill in the art will recognize that many modifications can be performed without deviating from the scope and spirit of the inventive concepts disclosed herein. Accordingly, the above description is not intended to be limiting upon the invention in any way.

What is claimed is:

1. A method for performing automated contact and information delivery over a network, said method comprising:
installing one or more interface devices at each of a doctor office and a medical facility;
establishing communication between each of the doctor office interface device, the medical facility interface device, and a site owner system;
displaying, via the doctor office interface, a call routing presentation screen;
receiving, at the doctor office interface, call routing preferences for the doctor office;
receiving, at the doctor office interface, message and receiver delivery preferences for each doctor office medical professional;
displaying, via the medical facility interface device, a connect on call presentation screen;
receiving, at the medical facility interface device, a plurality of call information selections;
identifying, via the site owner system, a medical professional based upon each of the call routing preferences, the message and receiver delivery preferences, and the plurality of call information selections;

displaying, via the medical facility interface device, the identified medical professional;

providing each of a textual contact mechanism and an audio/visual contact mechanism for establishing direct communication between the medical facility interface device and the identified medical professional;

generating, via the medical facility interface, at least one of a textual message and an audio/visual message; and delivering the generated message to the identified medical professional.

2. The method of claim 1, wherein one or more of the doctor office interface device, the medical facility interface device and the site owner system are purpose-built machines designed and configured solely to execute method steps for performing automated contact and information delivery.

3. The method of claim 1, wherein said call routing preferences comprises:

selecting a "call from" from the call routing presentation screen;

selecting a "call reason" from the call routing presentation screen; and selecting a "call type" from the call routing presentation screen.

4. The method of claim 3, wherein said "call from" is selected from a list comprising:

an emergency room, an ICU and other.

5. The method of claim 3, wherein said "call reason" is selected from a list comprising:

an admission, critical labs, code blue, new consult, family consult, fyi, medical reconciliation, need orders, other, patient care, pre-op clearance, need test results, room change notification, Cath and or STEMI, and stroke alert.

6. The method of claim 3, wherein said "call type" is selected from a list comprising:

an urgent IVR call, doctor to doctor, routine, STAT, and urgent.

7. The method of claim 3, wherein said call routing preferences further comprises:

selecting a medical professional from the call routing presentation screen to receive a message based on the selected "call from", the selected "call reason" and the selected "call type".

8. The method of claim 7, further comprising:

selecting default call information settings; and displaying the default call information settings on the connect on call presentation screen.

9. The method of claim 1, further comprising:

receiving a message hold instruction from the doctor office interface, said instruction including a future delivery time;

determining that the generated message is a textual communication and includes a "routine message";

holding the generated message until the future delivery time; and delivering the generated message at the future delivery time.

10. The method of claim 1, further comprising:

receiving a message forward instruction from the doctor office interface, said instruction including a different medical professional;

determining that the generated message is a textual communication and includes a "routine message"; and delivering the generated message to the different medical professional.

11. The method of claim 1, wherein said call information selections comprises:

selecting a "call from" from the connect on call presentation screen;

selecting a "call reason" from the connect on call presentation screen; and selecting a "call type" from the connect on call presentation screen.

12. The method of claim 11, wherein said "call from" is selected from a list comprising:

an emergency room, an ICU and other.

13. The method of claim 11, wherein said "call reason" is selected from a list comprising:

an admission, critical labs, code blue, new consult, family consult, fyi, medical reconciliation, need orders, other, patient care, pre-op clearance, need test results, room change notification, Cath and or STEMI, and stroke alert.

14. The method of claim 11, wherein said "call type" is selected from a list comprising:

an urgent IVR call, doctor to doctor, routine, STAT, and urgent.

15. The method of claim 11, wherein the identified medical professional changes based upon the selected "call from", the selected "call reason" and the selected "call type".

16. The method of claim 1, wherein said receiving message and receiver delivery preferences for each doctor office medical professional includes a plurality of personal contact details.

17. The method of claim 16, wherein said personal contact details include one or more of a medical professional's home telephone number, a cellular telephone number, an online telephone number, a pager number and a personal email address.

18. The method of claim 17, wherein said audio/visual contact mechanism includes displaying an audio/visual message icon adjacent to the identified medical professional.

19. The method of claim 18, wherein selection of the audio/visual icon initiates a voice call with the identified medical professional utilizing the personal contact details.

20. The method of claim 19, wherein the personal contact details are hidden from the user of the medical facility interface device.

* * * * *